United States Patent [19]

Baillie

[11] Patent Number: 4,809,543
[45] Date of Patent: Mar. 7, 1989

[54] APPARATUS AND METHOD FOR MONITORING ONE LIQUID IN ANOTHER

[75] Inventor: Lloyd A. Baillie, Plano, Tex.

[73] Assignee: Atlantic Richfield Company, Los Angeles, Calif.

[21] Appl. No.: 101,232

[22] Filed: Sep. 25, 1987

[51] Int. Cl.⁴ .................................. G01N 21/59
[52] U.S. Cl. .................................... 73/61.1 R
[58] Field of Search ................ 73/61.1 R; 356/436, 356/442

[56] References Cited

U.S. PATENT DOCUMENTS 4,102,177  7/1978  Okado et al. ............ 73/61.1 R X

FOREIGN PATENT DOCUMENTS 1032694  12/1964  United Kingdom ............ 73/61.1 R Primary Examiner—John Chapman
Assistant Examiner—Joseph W. Roskos
Attorney, Agent, or Firm—Michael E. Martin

[57] ABSTRACT

Oil and other contaminants entrained in a water flowstream may be measured to determine the concentration thereof by passing a sample of the flowstream through a vessel defining a chamber in which a light beam is projected to a photo sensitive element. Changes in light intensity caused by changes in concentration of oil or other contaminants are compared with the light intensity measured with a clarified or oil-free sample of liquid. A measuring system utilizes a centrifugal pump having a restricted fluid outlet to provide for thoroughly dispersal of the oil in the liquid flowstream. An alternate source of liquid may include a source of clear water or a source of clarified water which has been held in a holding tank to allow oil to separate from the water sample. The system is adapted for measuring the concentration and absorportion coefficient of oil entrained in a water flowstream such as refinery waste water streams, produced water streams from oil field flooding operations and the like.

13 Claims, 1 Drawing Sheet

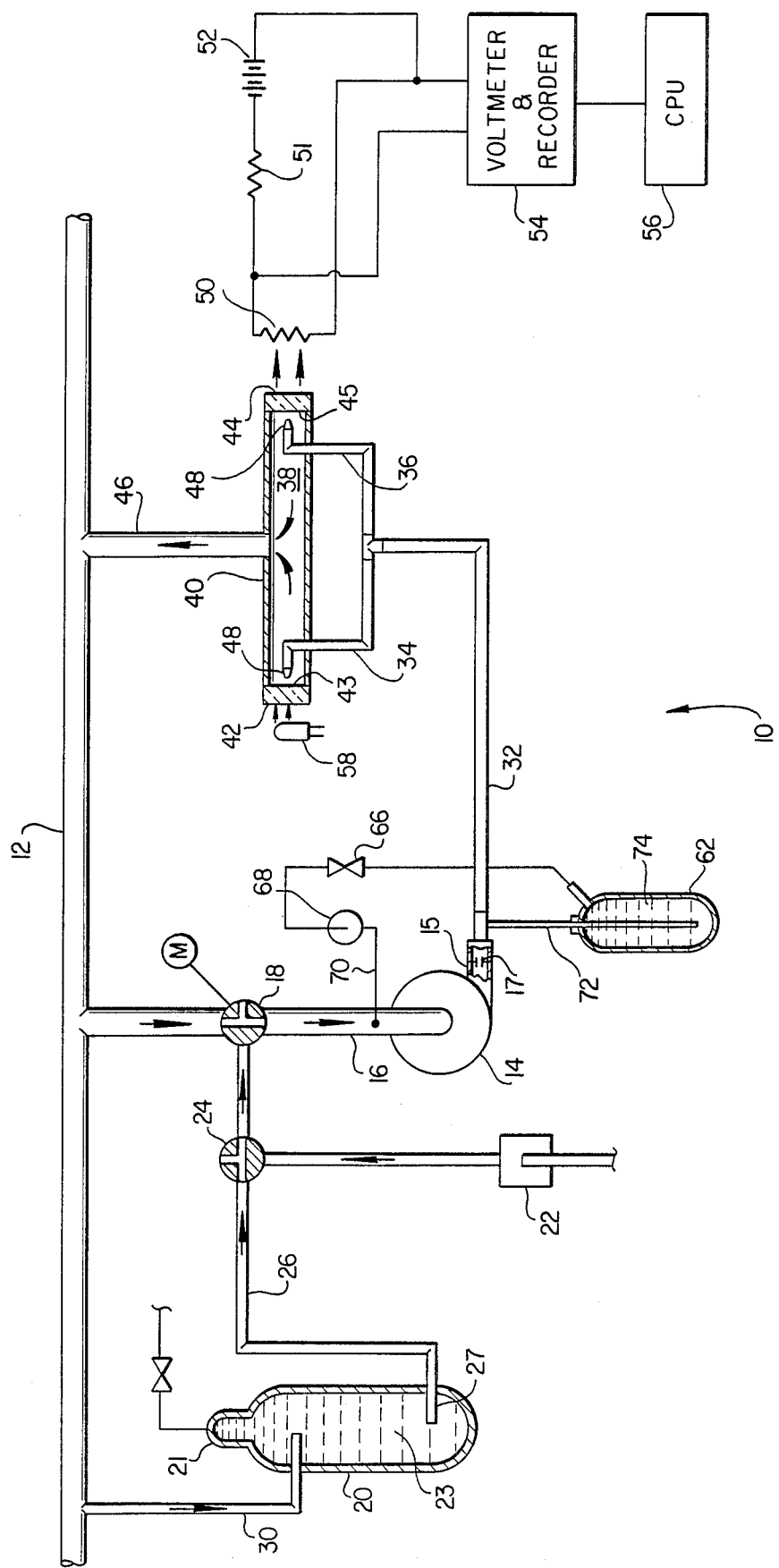

ically continuous basis. The time required for periodic sampling and remote analysis of a water flowstream which may contain varying amounts of oil is often excessive with respect to providing suitable monitoring and adjustment of related operations. Accordingly, there has been a strongly felt need for an apparatus or system which can monitor, on a substantially continuous basis, at least relative amounts of oil entrained in a water flowstream and, in particular, a water flowstream which may contain other contaminants wherein the oil contamination must be identified in spite of the presence of other contaminants. It is to this end that the present invention has been developed.

SUMMARY OF THE INVENTION

The present invention provides an improved apparatus or system for monitoring the presence of a liquid such as oil, including crude oil or the like, entrained in another liquid such as a water flowstream. In accordance with one important aspect of the invention an apparatus is provided which operates on a light attenuation principle for measuring the relative amounts of oil present in a water flowstream. By measuring the variation in light transmission through a continuous stream of water, in which oil has been thoroughly dispersed, utilizing a photosensitive electrical circuit a relatively accurate and sensitive system can be provided for monitoring changes in the oil content of a water flowstream, for example.

In accordance with another important aspect of the present invention, an apparatus is provided for monitoring the amount of oil entrained in a water flowstream wherein the water flowstream may have other contaminants which affect the clarity of the water and wherein a comparison may be made between clarified, substantially oil-free water and water containing varying amounts of oil as detected by sampling the flowstream. The present invention also provides a system for monitoring oil entrained in water wherein oil may be added to clarified or clear water to calibrate the system from time to time.

Further in accordance with the present invention, a system or apparatus is provided for monitoring oil entrained in water wherein the dispersement of the oil within the water flow steam is enhanced to improve the accuracy of the measuring process and a measuring chamber is provided with an improved arrangement of means for introducing the water flowstream into the chamber in a way in which errors in the operation of the light attenuation measuring system are substantially eliminated.

Still further in accordance with the present invention, there are provided improved methods for measuring the oil concentration in a water flowstream and the light absorption coefficient of the specific type of oil being measured. Still further, the mean particle radius of the oil droplets or particles in the water flowstream may also be determined from the measurements taken by the monitoring system.

Those skilled in the art will recognize the above described features and advantages of the present invention as well as other superior aspects thereof upon reading the detailed description which follows in conjunction with the drawing.

BRIEF DESCRIPTION OF THE DRAWING

The drawing FIGURE is a schematic diagram of a system for monitoring one liquid in another, such as oil entrained in water, in accordance with the present invention.

DESCRIPTION OF PREFERRED EMBODIMENTS

In the description which follows like parts are marked throughout the specification and drawing with the same reference numerals, respectively. The drawing FIGURE is in schematic form with conventional elements being shown for the most part by standard graphic symbols for such elements.

Referring to the drawing FIGURE, the system for monitoring the relative amount of oil entrained in water is generally designated by the numeral 10 and is adapted to continuously or intermittently sample liquid being conducted through a pipeline 12 for example. The system 10 includes a centrifugal pump 14 which is adapted to have its inlet conduit 16 connected to the pipeline 12 for withdrawing a sample of water therefrom or, alternatively, to a source of clarified or clear water by way of a valve 18. The valve 18 may be motor operated with a timer control so that at periodic intervals the pump 14 draws water from a clarified water tank 20 or from a source wherein the water has been clarified to the point of being clear by way of a positive displacement pump 22. A selector valve 24 is interposed in a conduit 26 for selectively placing the pump 14 in communication with the clarified water tank 20 or the pump 22.

In certain applications of the system 10, the water or other liquid being monitored for the quantity of oil or similar contaminant entrained therein may have other contaminants which are not to be considered for monitoring. In a system for monitoring the amount of oil entrained in water a sample of liquid is withdrawn from the pipeline 12 through a conduit 30 and allowed to settle in the tank 20 so that oil will rise to the tank collection dome 21 and somewhat clarified water may be withdrawn from the tank 20 through the conduit 26 which opens into the tank 20 at a bottom inlet conduit portion 27. In this way, as will be explained in further detail herein, clarified water may be measured by the apparatus 10 as a baseline measurement to compare the clarified water with that in which various amounts of oil may be entrained.

The pump 14 includes an outlet or discharge conduit portion 15 in which a throttling orifice 17 is interposed to increase the pressure and velocity of the liquid being discharged from the pump to a discharge conduit 32. The discharge conduit 32 is connected to two branch conduits 34 and 36 which open into a chamber 38 formed by a cylindrical sampling enclosure 40. The enclosure 40 is adapted to have light transmitting members or windows 42 and 44 disposed at opposite ends of the chamber 38. The enclosure 40 also has a fluid discharge conduit 46 which opens from the chamber 38 to the pipeline 12. The conduits 34 and 36 are each provided with a jet nozzle 48 disposed to eject a fluid stream on the interior surfaces 43 and 45 of the windows 42 and 44, respectively. A photoresistor 50 is adapted to be disposed directly adjacent to or on the window 44 and is in circuit with a fixed resistance 51, an electrical source 52 and a voltmeter and recorder 54. The voltmeter and recorder 54 is suitably connected to a central processing unit 56 for a purpose to be described in further detail herein. A light source 58 is disposed adjacent to the window 42 for directing a beam of light through the window 42, the chamber 38 and the window 44 to impact on the photoresistor 50.

The apparatus or system 10 is further provided with means for adding a predetermined quantity of oil or similar contaminant to the water or liquid flowstream entering the pump 14. A container 62 is arranged to have a discharge conduit 64 connected thereto and in circuit with a control valve 66 and a liquid droplet counter 68. A discharge conduit 70, leading from the droplet counter 68, is suitably connected to the pump inlet conduit 16 for adding a predetermined and measured quantity of oil or other liquid contaminant to the pump inlet flowstream. The vessel 62 is also in communication with the pump discharge conduit 32 by way of a branch conduit 72 which opens into the bottom portion of the interior chamber 74 of the vessel and which forms a source of pressure for forcing liquid in the chamber 74 through the conduit 64 and the droplet counter 68. The pressure differential across the pump 14 is sufficient to provide for circulation of oil stored in the chamber 74 to be metered into the conduit 16 so that controlled calibration of the photo sensitive element 50 may be carried out.

The operation of the system 10 may be conducted on a continuous or intermittent basis. Liquid may be continuously withdrawn from the pipeline 12 and conducted through the conduit 16 to the pump 14. The restricted flow through the pump 14 provided, in part, by the orifice 17 assures that the oil entrained in the water or added to the water is thoroughly dispersed due to the shearing action caused by the pump impeller. The oil-water mixture discharged from the pump 14 through the conduit 32 is ejected by the nozzles 48 directly on the light transmitting windows 42 and 44 to keep these windows clear by preventing the accumulation of any debris or oil film. Liquid is conducted back to the pipeline 12 through the conduit 46. Continuous readings of the voltage resulting from the change in resistance of the photoresistor 50 may be monitored by the voltmeter and recorder 54 and the concentration of oil in the water may be computed by the central processing unit 56 by solving one or more of the equations given hereinbelow.

When it is desired to calibrate the apparatus 10, the source of liquid to the pump inlet 16 may be switched to the pump 22, if clear water is to be used as the calibration basis, or, in the event that other contaminants are present in the water, the presence of which is not desired to be monitored, a quantity of water may be stored in the vessel 20 to allow the oil to separate so that so-called clarified water is retained in residence in the vessel interior chamber 23. Water may be withdrawn from the chamber 23 by way of the conduit 26, the valve 24 and the valve 18 to the pump inlet 16 during periods when the so-called baseline or reference liquid clarity is being determined. By making the vessel 20 of sufficient size that the contents are allowed to settle and the liquid become clarified substantially all of the oil may rise to the oil storage dome 21. This oil may be conducted to the vessel 62, for example, for use in further calibrating the system 10 by injecting predetermined quantities of oil into the pump inlet 16.

Light transmission through the chamber 38 obeys Beer's Law:

$$I/I_o = e^{-ACX} \tag{1}$$

Where A is the specific cross section of light absorbing or scattering particles in the liquid in centimeters squared per gram; C is the weight concentration of particles in the liquid in grams per centimeters cubed; and X is the path length of the light beam in centimeters. $I/I_o$ is the ratio of light intensity with the sample fluid being tested in the chamber 38 to the light intensity with clear or clarified water in the chamber 38. $I/I_o$ is the same as $R_o/R$, since the resistance of the photoresistor 50 is inversely proportional to light intensity. In a circuit where the photoresistor 50 is connected in series to the source 52 of fixed voltage E and fixed resistance 51, the ratio $R_o/R$ can be calculated from the voltage signal S measured with the sample fluid and the voltage signal $S_o$ measured with clear or clarified liquid as follows:

$$R_o/R = S_o(E-S)/S(E-S_o) \tag{2}$$

If the oil weight concentration C is known, the specific cross section, or also known as absorption coefficient, A applicable to the specific type of oil used may be found as follows:

$$A = -\ln(R_o/R)/CX \tag{3}$$

If the absorbing particles are black then the specific cross sectional area A can be used to find the mean particle radius r:

$$r = \tfrac{3}{2}Ad \tag{4}$$

where d is particle density.

For operation of the system 10 to determine the specific cross section or absorption coefficient A of a particular type of oil or oil mixture, the oil may be added to the flowstream entering the chamber 38 by way of the droplet counter 68 and the pump 14. Knowing the flow rate of liquid from a source of clarified liquid or clear liquid as hereinbefore described, oil may be added at a particular rate so that its concentration in the flowstream is known and the resistance for the clarified or clear liquid $R_o$ and the resistance R for the known concentration C of oil determined from equation (2). The path length of light, X, passing through the chamber 38 may be measured and thus the above recited equation (3) solved to determine the absorption coefficient A. Since the action of the pump 14 to shear the oil droplets may have some effect on the absorption coefficient A, the pump should be operated at a constant speed during determination of this parameter.

In the system 10 it is desired to measure the oil concentration by comparing the voltage measured by the voltmeter and recorder 54 with the voltage measured based on a clear or clarified liquid sample which is free of oil. Accordingly, the concentration of oil C may be derived from the equation:

$$C = -(1/AX)\ln\frac{S_o(E-S)}{S(E-S_o)} \quad (5)$$

Where $S$ and $S_o$ are the voltage signals measured for the liquid sample and the baseline or reference liquid sample such as clear or clarified water, respectively. This equation can be solved by the central processing unit 56 to give more or less continuous readings of the concentration of oil or a similar contaminant in a water or similar liquid being measured by the system 10.

In a preferred mode of operation of the system 10 the pump 14 may be adapted to draw a sample directly from the pipeline 12 on a continuous basis. Periodically, perhaps five minutes per hour, the valve 18 may be moved to draw a clear or clarified liquid sample from either the source 22 or the vessel 20, respectively. If clarified water is withdrawn from the chamber 23, the system will measure the concentration of suspended oil which is separated from the water by a period of clarification permitted by storage of water in the chamber 23. Oil present as a true solution and other contaminants would not be measured. Separated oil collected in the chamber 23 could be conveyed to the vessel 62 and periodically oil could be reintroduced into the pump inlet through the droplet counter 68 to provide an accurate measure of the oil light absorption coefficient. The automatic baseline determination plus calibration using separated oil should provide an accurate measurement of the concentration of the suspended oil phase in water being conducted through the pipeline 12.

Although a preferred embodiment of the invention has been described in detail, those skilled in the art will recognize that various substitutions and modifications may be made to the embodiment described without departing from the scope and spirit of the invention as recited in the appended claims.

What is claimed is:

1. Apparatus for measuring the concentration of an oil entrained in a liquid such as water flowing through a source such as at least one of a pipeline and vessel, said apparatus comprising:
   pump means having an inlet conduit adapted to be in communication with said source of liquid to be measured, said pump means including a discharge conduit;
   means forming a chamber for receiving a flow of liquid from said pump means including various amounts of said oil;
   a source of light adapted to project a light beam within said chamber;
   photosensitive means adapted to be positioned to receive a light beam from said source of light through said chamber;
   means for measuring an electrical signal from said photosensitive means related to the intensity of light conducted through liquid flowing through said chamber; and
   means for providing a quantity of clarified liquid free of said oil to said chamber for comparing the intensity of a light beam transmitted through said clarified liquid with a light beam transmitted through liquid including said oil.

2. The apparatus set forth in claim 1 wherein:
   said means for providing said clarified liquid includes a vessel adapted to be in communication with said source of liquid for storing a quantity of liquid to separate oil therefrom.

3. Apparatus for measuring the concentration of a liquid contaminant such as oil entrained in a liquid such as water flowing through a source such as at least one of a pipeline and vessel, said apparatus comprising:
   pump means having an inlet conduit adapted to be in communication with said source of liquid to be measured, said pump means including a discharge conduit;
   means forming a chamber for receiving a flow of liquid from said pump means including various amounts of said liquid contaminant, said means forming said chamber including first and second windows spaced apart one from the other;
   a source of light adapted to project a light beam within said chamber and through said windows;
   photosensitive means adapted to be positioned to receive a light beam from said source of light through said chamber and to provide an electrical signal responsive to the intensity of said light beam;
   means for injecting liquid into said chamber and in such a way as to cause a flow of liquid along the surfaces of said first and second windows to minimize errors in reading the light intensity caused by accumulations of contaminants on the surfaces of said windows, respectively; and
   means for measuring said electrical signal to determine the concentration of said liquid contaminant in the liquid flowing through said chamber.

4. Apparatus for measuring the concentration of a liquid contaminant such as oil entrained in a liquid such as water flowing through a source such as at least one of a pipeline and vessel, said apparatus comprising:
   pump means having an inlet conduit adapted to be in communication with said source of liquid to be measured, said pump means including a discharge conduit;
   means forming a chamber for receiving a flow of liquid from said pump means including various amounts of said liquid contaminant;
   a source of light adapted to project a light beam within said chamber;
   photosensitive means adapted to be positioned to receive a light beam from said source of light through said chamber and said liquid and to provide an electrical signal responsive to the intensity of said light beam;
   means for measuring said electrical signal to determine the concentration of said liquid contaminant in the liquid flowing through said chamber;
   a source of clear liquid; and
   means for placing said source of clear liquid in communication with said pump means for pumping clear liquid to and through said chamber whereby the level of light intensity through said clear liquid is measured by said means for measuring.

5. Apparatus for measuring the concentration of a liquid contaminant such as oil entrained in a liquid such as water flowing through a source such as at least one of a pipeline and vessel, said apparatus comprising:
   pump means having an inlet conduit adapted to be in communication with said source of liquid to be measured, said pump means including a discharge conduit;

means forming a chamber for receiving a flow of liquid from said pump means including various amounts of said contaminant;

a source of light adapted to project a light beam within said chamber;

photosensitive means adapted to be positioned to receive a light beam from said source of light through said chamber and to provide an electrical signal responsive to the intensity of said light beam;

means for measuring said electrical signal to determine the concentration of said contaminant in the liquid flowing through said chamber;

a vessel for holding a quantity of liquid from said source to clarify said liquid by separation of said contaminant from said liquid;

a conduit for placing said vessel in flow communication with said pump means; and means for selectively conducting clarified liquid from said vessel through said pump means and said chamber for comparing clarified liquid with liquid containing said contaminant whereby the change in light intensity measured by said means for measuring is based on comparing the light intensity transmitted by said liquid with said contaminant and with said clarified liquid, respectively.

6. Apparatus for measuring the concentration of a liquid contaminant comprising oil entrained in a liquid such as water flowing through a source such as at least one of a pipeline and vessel, said apparatus comprising:

pump means having an inlet conduit adapted to be in communication with said source of liquid to be measured, said pump means including a discharge conduit;

means forming a chamber for receiving a flow of liquid from said pump means including various amounts of said oil;

a source of light adapted to project a light beam within said chamber;

photosensitive means adapted to be positioned to receive a light beam from said source of light through said chamber and to provide an electrical signal responsive to the intensity of said light beam;

means for measuring said electrical signal to determine the concentration of said liquid contaminant in the liquid flowing through said chamber;

a source of oil; and means for conducting a measured quantity of oil to the inlet of said pump means for calibrating the measurement of change in light intensity by said means for measuring.

7. Apparatus for measuring the concentration of a liquid contaminant such as oil entrained in a liquid such as water flowing through a source such as at least one of a pipeline and vessel, said apparatus comprising:

pump means having an inlet conduit adapted to be in communication with said source of liquid to be measured, said pump means including a discharge conduit;

means forming a chamber for receiving a flow of liquid from said pump means including various amounts of said liquid contaminant;

means for restricting the flow of liquid from said pump means for thoroughly mixing said liquid contaminant and said liquid during the pumping thereof;

a source of light adapted to project a light beam within said chamber;

photosensitive means adapted to be positioned to receive a light beam from said source of light through said chamber and to provide an electrical signal responsive to the intensity of said light beam; and means for measuring said electrical signal to determine the concentration of said liquid contaminant in the liquid flowing through said chamber.

8. A method for determining the concentration of oil entrained in a liquid flowstream being conducted through one of a vessel, pipeline and the like, said method comprising the steps of:

providing means defining a chamber for receiving a sample of said liquid with oil entrained therein including means for transmitting light to a sensing element for measuring a change in light intensity transmitted through liquid in said chamber;

providing means in communication with said one of said vessel and said pipeline for conducting a sample of liquid flowing through said one of said vessel and said pipeline to said chamber;

conducting a sample of liquid from said one of said vessel and said pipeline to said chamber and measuring the change in light intensity with said sensing element;

conducting liquid from a source of clarified liquid wherein said clarified liquid is substantially devoid of said oil through said chamber;

measuring the light intensity sensed by said sensing element; and comparing the measurements of light intensity to determine the concentration of oil in said liquid flowstream.

9. The method set forth in claim 8, including the step of:

providing said source of clarified liquid by retaining a sample of liquid withdrawn from said one of said vessel and said pipeline in a holding vessel to provide for separation of said oil from said liquid.

10. The method set forth in claim 8 wherein:

said sensing element is disposed in an electrical circuit including means for measuring a change in voltage in said ciruit related to a change in light intensity sensed by said sensing element, and the concentration of oil, C, is determined from the equation:

$$C = -(1/AX)\ln \frac{S_o(E - S)}{S(E - S_o)}$$

where A is the specific cross section of light absorbing or scattering particles, X is the path length of the light beam, E is a fixed voltage from a source in circuit with said sensing element, S is the voltage signal measured across the sensing element for the liquid sample to be measured and $S_o$ is the voltage signal measured across the sensing element for clarified liquid in said chamber.

11. The method set forth in claim 8 wherein:

the specific cross section of light absorbing or scattering particles is determined by conducting liquid from a source of clarified liquid through said chamber and measuring the light intensity sensed by said sensing element;

adding oil to said clarified liquid at a known rate to provide a known concentration of oil in said clarified liquid and measuring the light intensity sensed by said sensing element; and comparing electrical signals from said sensing element when measuring the light intensity sensed of clarified liquid and liquid with oil therein, respectively.

12. The method set forth in claim 11 wherein:

the step of adding a known concentration of oil to said sample of liquid is carried out by introducing oil to said clarified liquid and passing said clarified liquid and added oil through pump means for shearing said oil to form oil droplets dispersed through said sample of clarified liquid.

13. A method for determining the concentration of oil entrained in a liquid flowstream being conducted through one of a vessel, pipeline and the like, said method comprising the steps of:

providing means defining a chamber for receiving a sample of said liquid with oil entrained therein including means for transmitting light to a sensing element for measuring a change in light intensity transmitted through liquid in said chamber;

providing means in communication with said one of said vessel and said pipeline for conducting a sample of liquid flowing through said one of said vessel and said pipeline to said chamber;

conducting a sample of liquid from said one of said vessel and said pipeline to said chamber and measuring the change in light intensity with said sensing element;

thoroughly dispersing said oil in said liquid before conducting said liquid to said chamber by providing a centrifugal pump for pumping liquid to said chamber; and throttling the flow of liquid being discharged from said pump before said liquid enters said chamber.

* * * * *